US007077868B2

(12) United States Patent
Perkins et al.

(10) Patent No.: US 7,077,868 B2
(45) Date of Patent: *Jul. 18, 2006

(54) ATTACHMENT SYSTEM FOR PROSTHESIS

(76) Inventors: Dale Perkins, 542 Addison Ave. W., Twin Falls, ID (US) 83301; Matt Perkins, 542 Addison Ave. W., Twin Falls, ID (US) 83301

( * ) Notice: Subject to any disclaimer, the term of this patent is extended or adjusted under 35 U.S.C. 154(b) by 0 days.

This patent is subject to a terminal disclaimer.

(21) Appl. No.: 10/746,208

(22) Filed: Dec. 23, 2003

(65) Prior Publication Data

US 2004/0138763 A1    Jul. 15, 2004

Related U.S. Application Data

(63) Continuation-in-part of application No. 09/972,729, filed on Oct. 4, 2001, now Pat. No. 6,666,894.

(60) Provisional application No. 60/238,301, filed on Oct. 4, 2000.

(51) Int. Cl.
*A61F 2/80* (2006.01)
(52) U.S. Cl. ....................................................... 623/36
(58) Field of Classification Search .................. 623/27, 623/32, 33, 36, 38, 53, 54, 57; 602/63
See application file for complete search history.

(56) References Cited

U.S. PATENT DOCUMENTS

| 694,325 | A | * | 2/1902 | Peer | 623/28 |
| 4,463,459 | A | | 8/1984 | Shorter et al. | 3/30 |
| 4,578,083 | A | | 3/1986 | Williams | 623/42 |
| 5,211,667 | A | * | 5/1993 | Danforth | 623/35 |
| 5,800,565 | A | | 9/1998 | Biedermann | 623/38 |
| 5,888,232 | A | | 3/1999 | Taylor | 623/38 |
| 6,706,364 | B1 | * | 3/2004 | Janusson et al. | 428/145 |

OTHER PUBLICATIONS

Article entitled "Clinical Application of Roll-on Sleeves for Myoelectrically Controlled Transradial and Transhumeral Prostheses," JPO 2000; vol. 12, No. 3, pp. 1-6. Exact publication date unknown, but believed to have been published sometime during the period of Jun.-Sep., 2000.
Advertisement for Icelock™ attachment system, OSSUR Product Catalogue 2000-2001, Jun. 2000, pp. E3-E4.

* cited by examiner

*Primary Examiner*—Corrine McDermott
*Assistant Examiner*—William Matthews
(74) *Attorney, Agent, or Firm*—Pedersen & Co., PLLC; Ken J. Pedersen; Barbara S. Pedersen

(57) ABSTRACT

An attachment system secures a residual limb to an artificial limb in a comfortable and substantially non-rotational manner. The attachment system offers proximal anchoring of the residual limb in a hard socket, by connecting a side surface of a residual limb liner to the side surface of the socket. Preferably, this connection is accomplished using an extension member extending from the liner through a portion of the socket interior, through the socket wall, and attaching to a latch mechanism. The preferred attachment system requires no clearance in the bottom of the socket well because neither the extension member nor the latch mechanism is located between the distal end of the residual limb/liner and the bottom of the well. The attachment system is preferably disposed entirely along the side of the limb and the side of the socket.

6 Claims, 9 Drawing Sheets

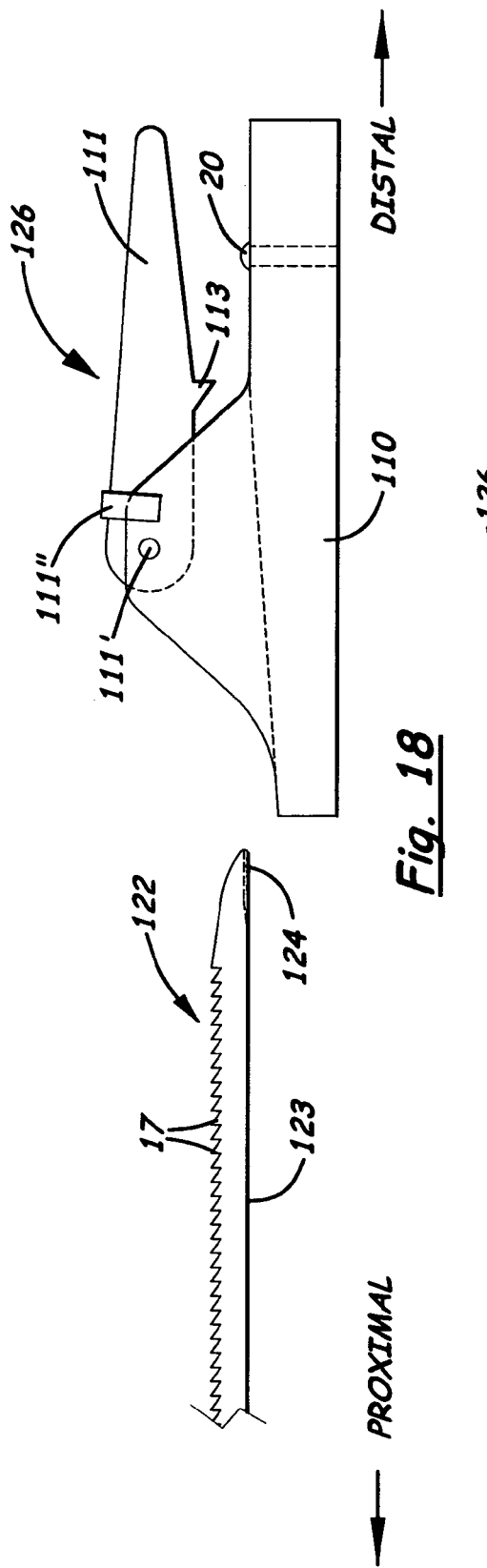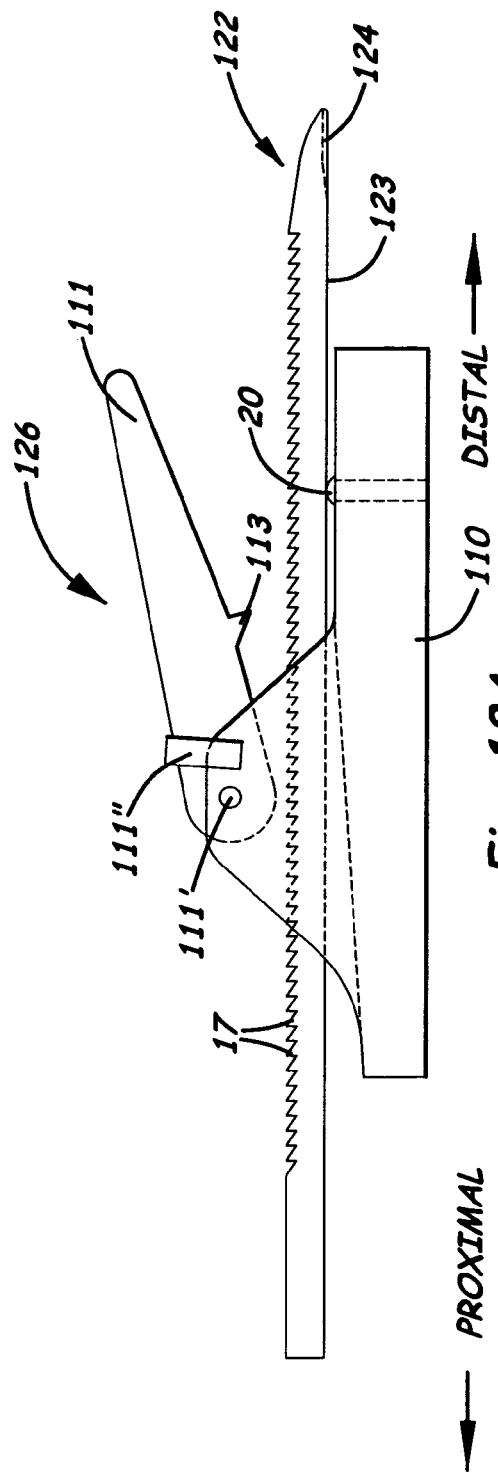

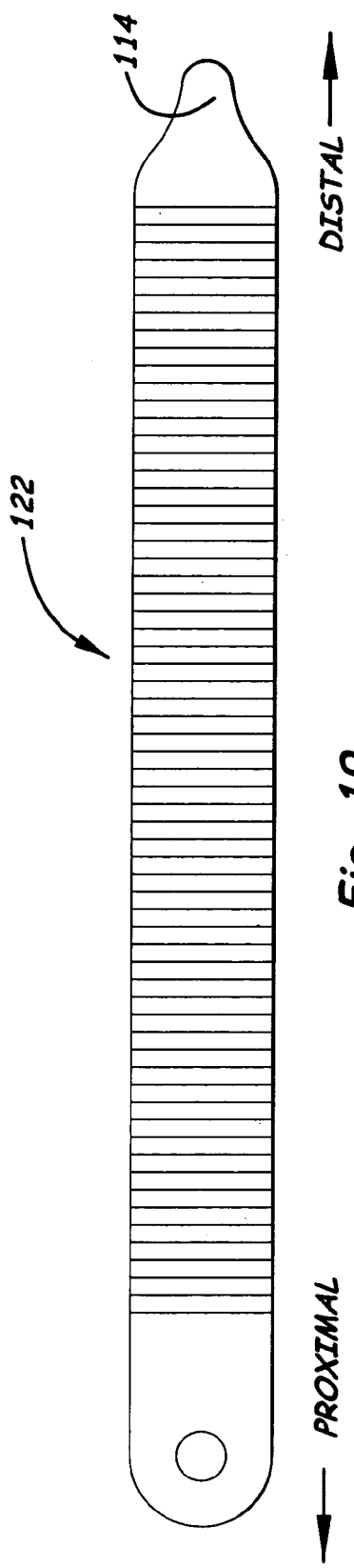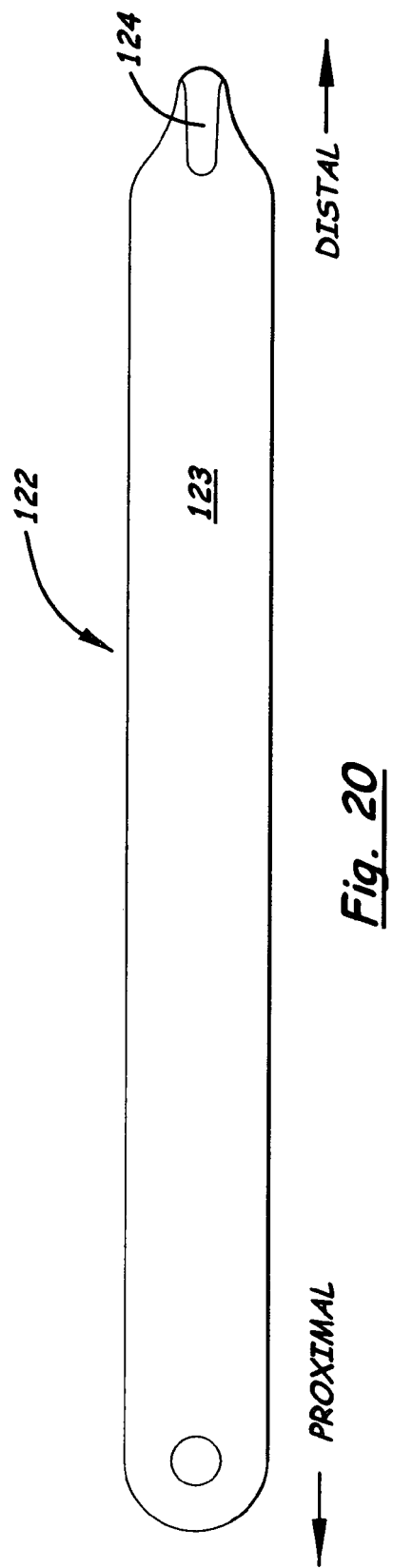

ATTACHMENT SYSTEM FOR PROSTHESIS

This application claims priority from U.S. Non-Provisional Patent Application Serial No. 09/972,729, filed on Oct. 4, 2001, entitled "Attachment System for Prosthesis," issuing on Dec. 23, 2003 as U.S. Pat. No. 6,666,894, which claims priority of U.S. Provisional Patent Application Ser. No. 60/238,301, filed on Oct. 4, 2000, entitled "Attachment System for Prosthesis," the disclosures of which are incorporated herein by this reference.

BACKGROUND OF THE INVENTION

1. Field of the Invention

The present invention relates generally to prosthetics, and, more specifically to an attachment system used in the donning/doffing of a socket onto a residual limb. The present invention more particularly relates to an attachment system that requires little or no clearance inside the socket between the socket and the residual limb, that controls rotation of the prosthesis, and that may be used with a suction-fit socket system. The invented attachment system extends from the side of a liner on the user's limb, through an aperture in the socket, to the outer side of the socket, substantially proximal on the limb and on the socket relative to conventional more "distal" attachment devices. Therefore, the invented attachment may properly be called an exterior, proximal attachment device for a prosthesis.

2. Related Art

For years, many different methods have been used to retain or "suspend" a prosthetic limb on an amputee's residual limb. Gravitational and other forces, for example, from movement of the limbs, tend to cause separation between the prosthetic limb and the patient's residual limb during use. This happens, for example, during the swing phase of gait, when a prosthetic leg is additionally subjected to centrifugal forces. Patients have routinely worn a variety of belts, straps, cuffs, and harnesses to retain their prosthetic limbs against separation from the limb during these periods. However, such devices are often inconvenient and may tend to cause chafing against the patient's body, giving rise to sores and abrasions.

The manner in which an artificial limb is suspended and/or attached to the residual limb determines the amount of control an amputee has over the prosthesis. Therefore, by improving suspension/attachment without adding weight and excessive mechanism, the amputee may obtain improved comfort, convenience, and suspension mobility.

A common approach to tackling this problem has led to the design of a roll-on suction liner, which is rolled onto the residual limb and attached at its distal end to a socket or artificial limb. The liner, which is usually fabricated from silicone, or some other gel form, fits snugly over the residual limb, preferably completely covering the distal end of the residual limb and extending for at least several inches to cover the entire circumference of the proximal region of the residual limb. The liner, in turn, is enveloped, especially at its distal end, by the socket of the prosthesis, which is also called a "hard socket." A suction fit is preferably formed between the hard socket and the liner. This suspension method is very advantageous for the amputee. It gives the amputee the ability to better control the prosthesis and provides for useful sensory or proprioceptive feedback. Suction suspension also makes a prosthesis feel lighter, compared to other forms of suspension. Unfortunately, only a small percentage of amputees can successfully and comfortably wear a liner without another form of suspension.

Therefore, the socket liner is typically equipped with a detachable component, at its distal end, which mates with a locking device in the interior of the socket at the bottom of the interior space or "well." This system secures the distal end of the, residual limb/liner to the distal end of the artificial limb socket well, and, hence, is called a "distal attachment." The locking device in the distal end of the socket well typically employs a spring-loaded clutch mechanism or a pin-lock mechanism. The component on the distal end of the liner is typically a cylindrical barb-shaped structure or frictionally-retained pin.

One problem associated with such designs is the tugging or pull on the distal end of the limb. Most of these locks are not air tight, thus allowing air to flow into the hard socket and to eliminate the "suction." When this happens, the only suspension is the pin, which is a traction suspension, rather than suction. In cases where prosthetic socks are worn outside the liner, there is a risk the user's limb will become trapped in the socket if the sock is caught in the locking device. In these incidents, most patients are forced to make emergency trips to their practitioner to remove the prosthetic. Also, the locking device and attachment component cooperate in such a way to permit the barb or pin to lock in a plurality of longitudinal positions, which affects the overall length of the prosthesis. This can make it difficult for the patient to consistently achieve the same prosthetic configuration when the residual limb and the artificial limb are articulated. It should be further noted that, by weight of the lock being added at the distal end of the residual limb or near the distal end of the socket, this can make the prosthetic device feel heavier because of a "lever arm" effect, than if the same weight were placed more proximally. Additionally, many amputees, whether because of the length of their residual limb or their height, do not have room in the suction liner-socket-prosthesis combination for a distal locking mechanism. Or, additionally, use of a distal lock may limit what other prosthetic components that patient may use.

Despite the large number of suspension options available, none of the above-mentioned devices act to eliminate rotation between the hard socket and the suction liner. In an attempt to alleviate the rotation problem, a design called a "quad socket" has been used for many years. The quad socket is shaped in a square manner more than a cylindrical manner, and forcing the "cylindrical" limb to fit tightly in this square receptacle makes the prosthesis less apt to rotate on the limb, much as if you made a wheel square. Unfortunately, this is not a very comfortable position for the limb. Today, there has been a trend toward more naturally-shaped sockets, making rotation control even more difficult.

Therefore, there is still a need for an improved attachment system for prosthetics. Also, there is a need for improving retention of the stump in the socket without sacrificing the patient's comfort and without comprising on expense, weight and simplicity of use of the prosthesis. There also is a need for improving rotation control, which will improve the patient's overall comfort and agility.

SUMMARY OF THE INVENTION

The present invention is an attachment system and methods for connecting a prosthesis to a residual limb of the user. Preferably, the attachment system extends from the side surface of a liner on a residual limb to the outside side surface of a hard socket fitted around the liner and limb. Preferably, the attachment system includes a strap system that connects to the outer side surface of the liner to the socket, wherein said strap extends into the socket along a portion the limb, and through an aperture in the sidewall of the socket. Preferably, the strap further extends to a buckle or other latch mechanism connected to the outer side surface of the socket, typically about midway or more, proximally, on the outside surface of the socket. The externally mounted buckle is easily reached and maintained by the user, and easily retrofit as an add-on feature to existing hard sockets. In this way, a combination of the invented prosthetic attachment system and suction fit provide superior retention of the artificial limb on the user.

The preferred strap system includes a disk member or "umbrella" that may be adhesively secured to the surface of the liner, and an elongated strap that extends distally from the umbrella and longitudinally a short distance along the side surface of the limb. The strap may be secured to the umbrella in such a way that its exact angle relative to the limb's longitudinal axis may be adjusted as desired and then locked in place, for example, by tightening of a bolt. The lock is preferably a buckle-style latch mechanism, with a spring-biased member and one or more sharp edges, that frictionally engage transverse detents located between transverse raised ridges on the strap's surface. Thus, the strap is inserted into the buckle to the extent desired by the user, and, in a ratchet-like action, the sharp edges wedge into the transverse detents and secure the strap from being pulled out or away from the buckle. Thus, the strap is anchored in the buckle, and the socket is held closely on the residual limb until the user chooses to unbuckle the buckle.

The especially preferred embodiment includes a duel strap and buckle system wherein one strap and one buckle are located on the medial surface of the liner and socket respectively and one strap and one buckle are located on the lateral surface of the liner and socket respectively. The especially preferred embodiment also includes the invented strap and buckle system wherein said strap may have a "nipple" shaped tab extension at its most distal end to facilitate the strap through the buckle. Also, the underside of the said strap may have a small grooved channel at its distal end in order to feed the strap over a rivet in the base of the buckle. The especially preferred buckle may include a spring-biased member with one or more sharp edges, that frictionally engage transverse detents located between transverse raised ridges on the strap's surface. In order to remove said strap from said buckle, the user pulls the distal end of the buckle away from the socket.

Therefore, the prosthetic attachment system is easily accessible, effective, simple, and easy to use. The versatility and simplicity, and non-interfering design of the invented prosthetic attachment system helps provide reliable and comfortable suspension for an artificial limb on a great number of persons with limb deficiency.

BRIEF DESCRIPTION OF THE DRAWINGS

FIG. 18 is a detail side view of the strap of FIGS. 13–17 in relation to the buckle of FIGS. 13–17, before the strap is inserted in the buckle.

FIG. 18A is a detail side view of the strap of FIGS. 13–18 in relation to the buckle of FIGS. 13–18, after the strap is inserted in the buckle.

FIG. 19 is a top view of the especially preferred embodiment of the strap of FIGS. 13–18.

FIG. 20 is a bottom view of the especially preferred embodiment of the strap FIGS. 13–19.

DETAILED DESCRIPTION OF THE INVENTION

Referring to the Figures, there is shown one preferred embodiment and the especially preferred embodiment, but not all embodiments, of the present invention, which is referred to herein as an attachment system. In this Description and the Claims, the term "proximal" means toward the center/torso of the body, and so toward the top/upper end of the liner and prosthetic device. Thus, in the case of a prosthetic device for a person's leg, "proximal" would mean nearer or toward the upper thigh and trunk. "Distal" means away from the center/torso of the body, and so the regions of the liner or prosthetic device farther out from the trunk, farther out on the leg.

Figure 8:
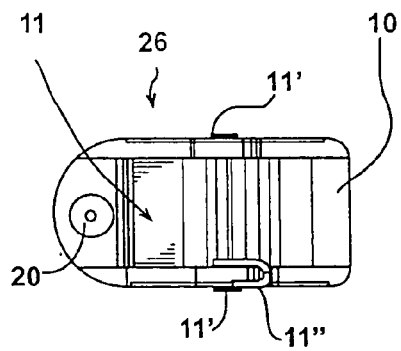
FIG. 8 is a top view of the buckle of FIG. 6.
Figures 9, 10:
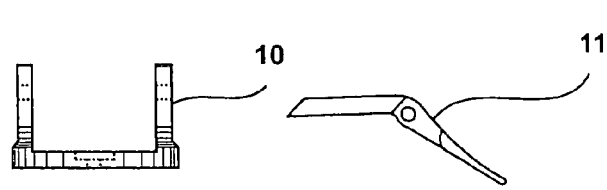
FIG. 9 is a frontal view of the base frame of the buckle of FIGS. 6 and 8.
FIG. 10 is a side view of one embodiment of the lever of the buckle of FIGS. 6 and 8.
Figure 11:
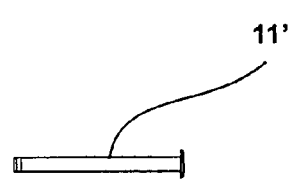
FIG. 11 is a frontal view of the pin of the buckle of FIGS. 6-10.
Figure 12A:
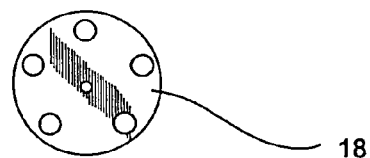
FIG. 12A is a plan view of one embodiment of an umbrella plate for attachment to an outside surface of a liner.
Figure 12B:
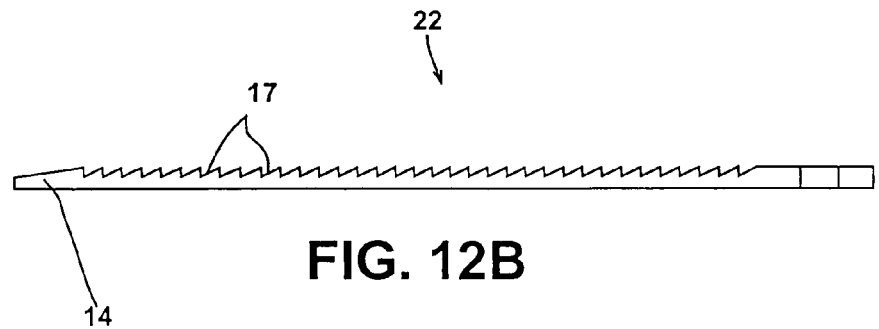
FIG. 12B is a side view of one embodiment of a strap according to the invention, for cooperating with, and connecting, the buckle-style lock and the umbrella plate.

The preferred buckle 26 or latch mechanism of the invented attachment system includes base 10, which is mounted on the external surface of the hard socket 12 by means of a rivet 20, glue or other fastener, or it may even be molded integrally with the socket 12. The buckle 26 is positioned proximally higher up the socket than conventional "distal" locks that are mounted near the distal end of the socket, typically at the bottom of the inside "well" of the hard socket 12. Connected to base 10 are a lever 11 and pin 11' with e-clips 11", which together create a biased system for receiving and capturing strap 22, as seen in FIGS. 8 and 12B. Strap 22, as discussed below, is preferably secured to the liner 16, by means of a umbrella 18 (see FIG. 12A), and is long enough to comfortably and conveniently extend from the middle to upper region of the side of the liner to reach the lower region of the liner (see FIG. 2).

Liner 16 may be a custom or a pre-manufactured liner as described in the Related Art section above. Examples of currently-available conventional liners are ICEROSS, ALPHA, LUXURY LINER, ALPS, SILIPOS (all trademarks). Modern urethane liners are especially preferred.

Figure 2:
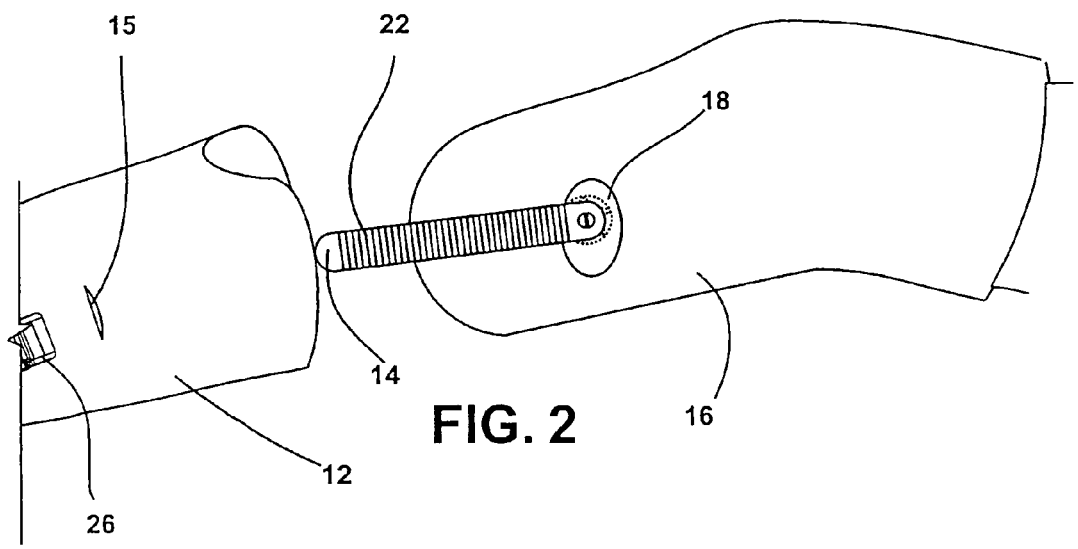
FIG. 2 is a lateral view of the preferred prosthetic attachment system showing the strap as it enters the inside of the socket.

Strap 22 is connected at its proximal end to liner 16, preferably by an umbrella 18 or other fixture or bracket. The umbrella 18 may be glued to the liner, as seen in FIG. 2. Umbrella 18, as shown in FIG. 12A, is preferably an aluminum plate structure of approximately ¾" in diameter and ¼" thick, with preferably a slightly-concave inner surface for contacting the glue, and with apertures at various locations on the umbrella to assist in receiving and better gripping of the glue that connects the umbrella 18 to the liner's 16 outside side surface. However, umbrella 18 may also be sewn onto or into liner 16, or it may be formed integrally with liner 16. Also, alternatively, other shapes of an attachment plate or other attachment means may be used instead of the umbrella, as long as preferably they are thin and easily slide/fit into the socket.

The strap 22 is attached to the umbrella 18, for example, with a 10/24-spanner bolt or screw. The screw is then tightened down to the umbrella 18, rather than allowing the strap 22 to pivot around the screw. This results in the strap 22 being adjustable, allowing the user or prosthetist to move the strap 22 and then lock it into the optimum position, even if the strap 22 or lock mechanism have been attached to their respective structures in less-than-perfect position or location.

Figure 1:
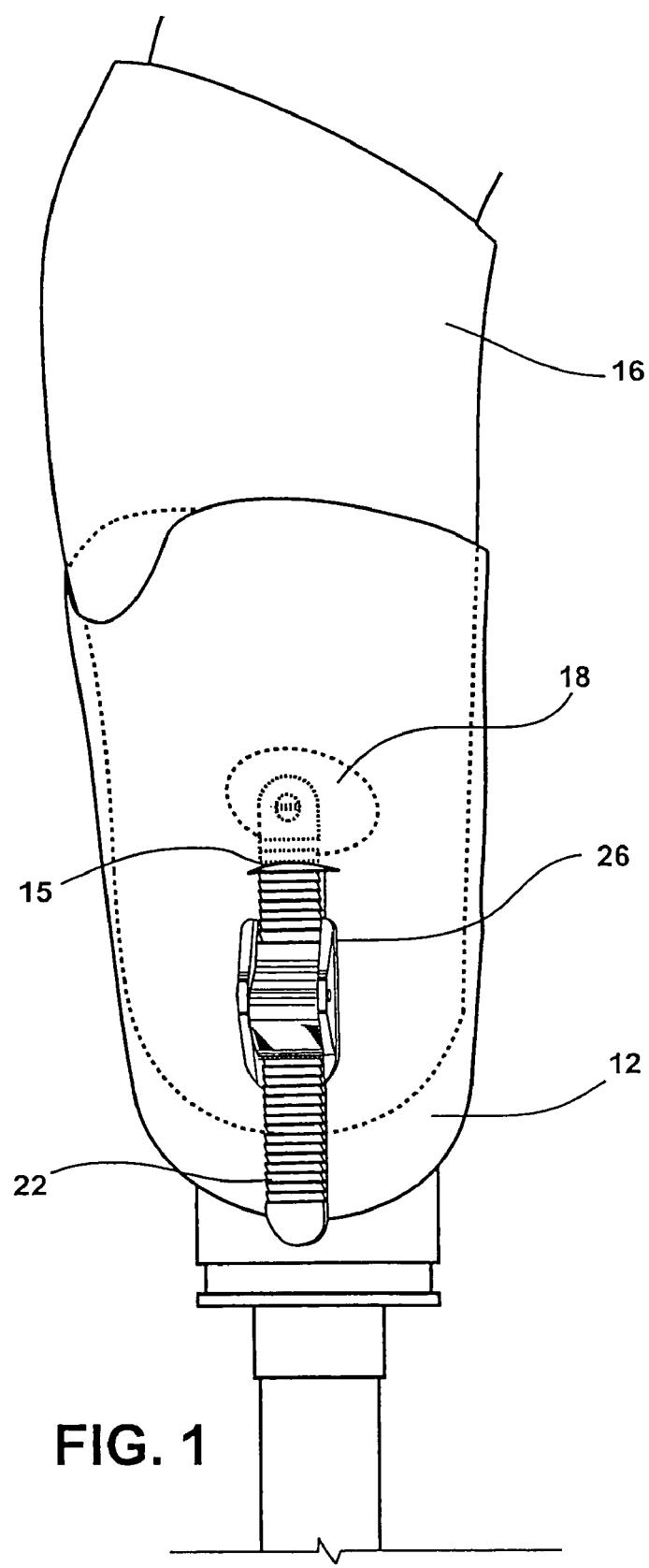
FIG. 1 is a close-up, lateral view one embodiment of the prosthetic attachment system according to the invention, installed on a user's residual limb.
Figure 3:
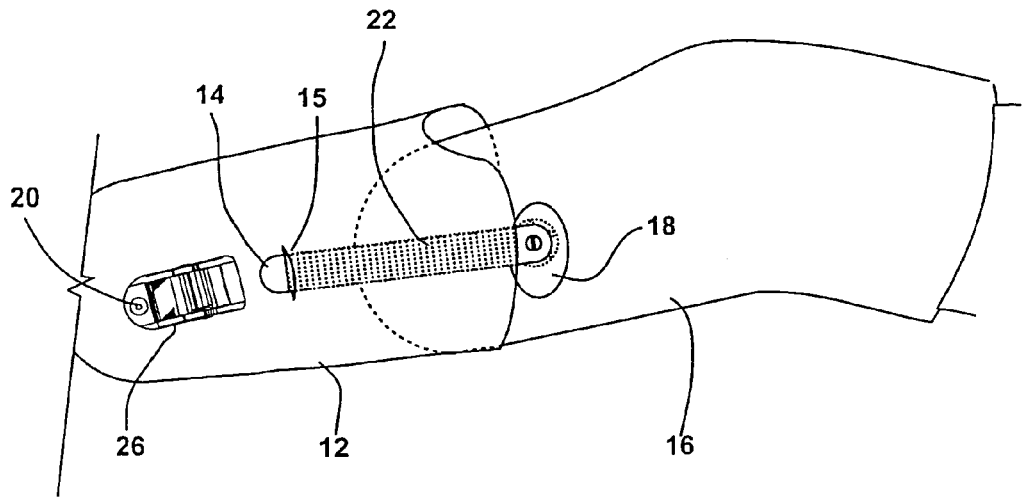
FIG. 3 is a lateral view of the preferred prosthetic attachment system showing the strap after it has entered the socket and as it passes through an opening in the socket to the socket's outer surface.
Figure 4:
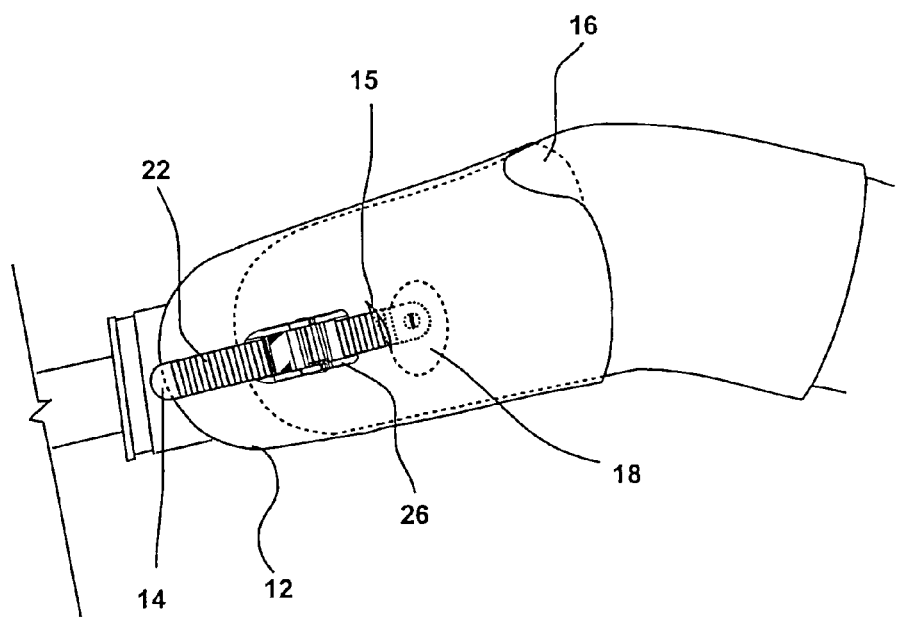
FIG. 4 is a lateral view of the preferred prosthetic attachment system showing the strap after it has entered the buckle.
Figure 5:
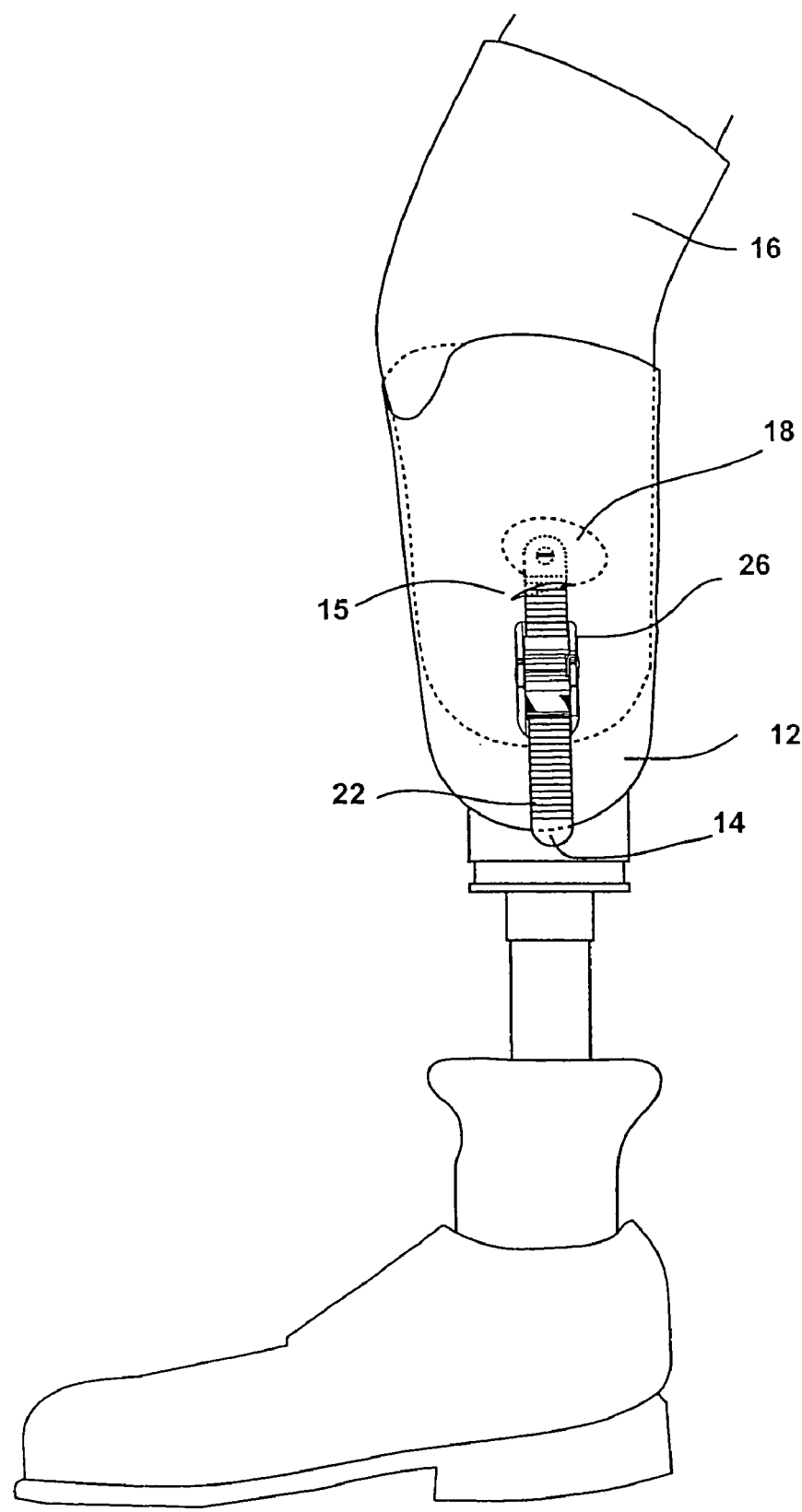
FIG. 5 is a lateral view of the preferred embodiment after the prosthetic is installed on the user's residual limb, showing the foot.
Figure 6:
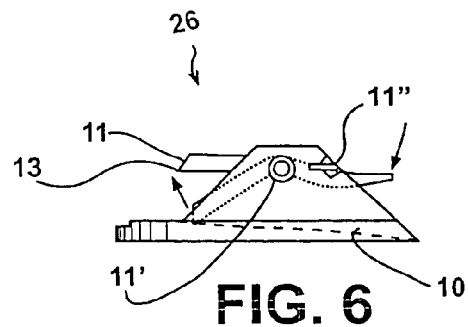
FIG. 6 is a side view of one embodiment of the buckle-style latch mechanism of the present invention.

When hard socket 12 is installed on the residual limb, it extends up over and around liner 16 and umbrella 18, as shown in FIG. 1. Strap 22 extends from umbrella 18 on liner 16 a short distance on the inside of socket 12 through an aperture 15 in socket 12 to the external surface of socket 12 (see FIGS. 2 and 3). There, the strap 22 continues to extend to and through the preferred buckle 26 attached on the outside surface of the socket 12, as shown in FIG. 4. The buckle 26 adjustably receives the distal end of the strap 22, by means of the strap 22 extending through the buckle 26 between the base 10 and the lever 11. The strap 22 is pushed/pulled through the buckle 26 to the point where the hard socket 12 is securely, but comfortably secured around and connected to liner 16 via the strap 22 and umbrella 18 combination. This way, the advantages of the invention are realized.

Strap 22 is preferably sufficiently rigid, sufficiently long, and is positioned so that, upon the limb/liner being inserted into the socket, the strap naturally tends to slide to and through the aperture 15, to the buckle 26, and through the buckle 26 with little or no need for the user to thread or pull the strap 22 through the aperture 15 or buckle 26. A prosthetist will be able to adjust the strap and/or buckle locations and aperture size to enable this smooth movement and latching of the strap in the buckle. Optionally, the socket wall surface, on the interior or exterior, may be contoured to facilitate and direct the strap.

Figure 7:
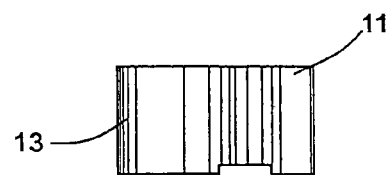
FIG. 7 is a top view of the lever of the buckle of FIG. 6.

The release button of the buckle 26 is buckle lever 11, which features sharp edge 13, as shown in FIG. 7. The top surface of base 10 ramps up in thickness in the distal direction. This provides for easier strap 22 entry into the buckle-style latch mechanism, and increasing pressure on the strap 22 when engaged by means of the buckle lever 11 pressing/ratcheting against the strap 22. Edge 13 engages the sharp "ratchet teeth" of strap 22, extending into the transverse detents 17 and abutting against the teeth walls upending from the strap top surface (see FIG. 12B). Any pull on the strap 22 in the proximal direction is resisted by the engagement of edge 13 in detents 17 and the pressure of lever 11 against e-clips 11". The attachment system may be placed in a position on the liner and socket that the prosthetist deems most advantageous and convenient for the patient. The mechanism is attached to the exterior of the socket at a location determined by test socket fitting, but in any event, not at the distal end of the socket. Typically, when a single attachment system is employed, it will placed in a lateral position so that the user may reach it by reaching toward the outside of his limb.

After mounting of the base 10 of the buckle 26 onto the socket 12, the umbrella 18 onto the liner 16, and strap onto the umbrella 18, the roll-on prosthetic liner 16 of choice is applied to the patient. The patient can then step into the hard socket 12 and engage the attachment system, by inserting the strap 22 through the aperture 15 and into the buckle 26. This procedure may be used in the retrofitting of the attachment system to an existing prosthetic.

If a new prosthetic is being created, the liner 16 is applied to the patient, and the ideal location for the umbrella 18 is marked on liner 16. A mold over the patient's limb and liner 16 is then taken. After the mold and liner 16 are removed, the umbrella 18 is then attached to the liner 16 in the location marked. From the mold the hard socket 12 is created, and the base 10 of the lock mechanism is attached in the proper location on the outside of hard socket 12, and then the aperture 15 is created in hard socket 12 as above.

The aperture 15 or any other opening through the socket preferably may be easily sealed by a gel suction wrap/cover, or other air-tight wrap or plug that preferably encases the lock mechanism and aperture. This allows and maintains a "suction" fit between the socket and the liner that improves the function of the prosthetic.

EXAMPLE

The above attachment system was fit to three test patients. All three of these patients utilized ALPHA™ liners in a normal manner. The locking tab was attached to the ALPHA™ liners in a normal manner. Two of these patients were unilateral transtibial amputees, and one patient was a unilateral congenital above-knee amputee. The above-knee amputee was a congenital amputation resulting from PFFD, and his amputation level was consistent with a knee disarticulation level. All three of these patients either demonstrated problems with conventional distal pin-lock systems, or, in the case of the transfemoral amputee, did not have sufficient room to install any of the distal locking mechanisms currently on the market. These patients were using the prosthetic lock suspension according to the present invention on their prosthesis on a daily basis. These patients were all experimentally fit in June of 2000 and no problems were encountered with mechanical failures or with patient acceptance or satisfaction. We continue to monitor these patients at 2–3 week intervals.

One may see, after reviewing the disclosure of this Description and the Drawings, that the invented attachment system tends to prevent rotation of the prosthesis on its longitudinal axis (axis extending between its proximal end and distal end) relative to the amputated limb. By providing one of the invented side-located, "proximally-located" attachment systems, such rotation is limited or prevented. This is because strap extends from a fixed anchor location on the side of the liner/limb to a fixed anchor location on the side of the socket, thus connecting those two fixed locations together at substantially a fixed distance apart, thereby not allowing the anchor location on the socket to rotate any significant distance away from the anchor location on the liner. Although one of the invented attachment systems is preferred, more than one may possibly be used, for example, at two positions around the side of the limb/socket, as described below in the Especially Preferred Embodiment section.

Other benefits of the attachment system include comfort and ease of use. The preferred attachment system is simple to use, each to reach, and requires a minimum of dexterity. The externally-mounted lock mechanism eliminates the jamming of conventional distal locks often caused by a sock worn over the roll-on liner.

While a ratchet-style buckle and strap combination is preferred, other releasable attachments and fasteners may be used. For example, extension members other than a flat strap with detents may be used, such as a cord(s), loop(s), tab(s), or other rigid or flexible extension members. Latch mechanisms other than a buckle may be used, such as a hook(s), clip(s), snap(s), or other devices that adjustably or non-adjustably grip the extension member. The connection between the extension member and the latch mechanism is preferably, but not necessarily, adjustable. This permits the user or the prosthetist to manipulate the connection for optimum use and comfort, either by lengthening or shortening the connection or by pivoting or otherwise moving the location of the extension member or latch mechanism.

AN ESPECIALLY PREFERRED EMBODIMENT

Figures 13, 14:
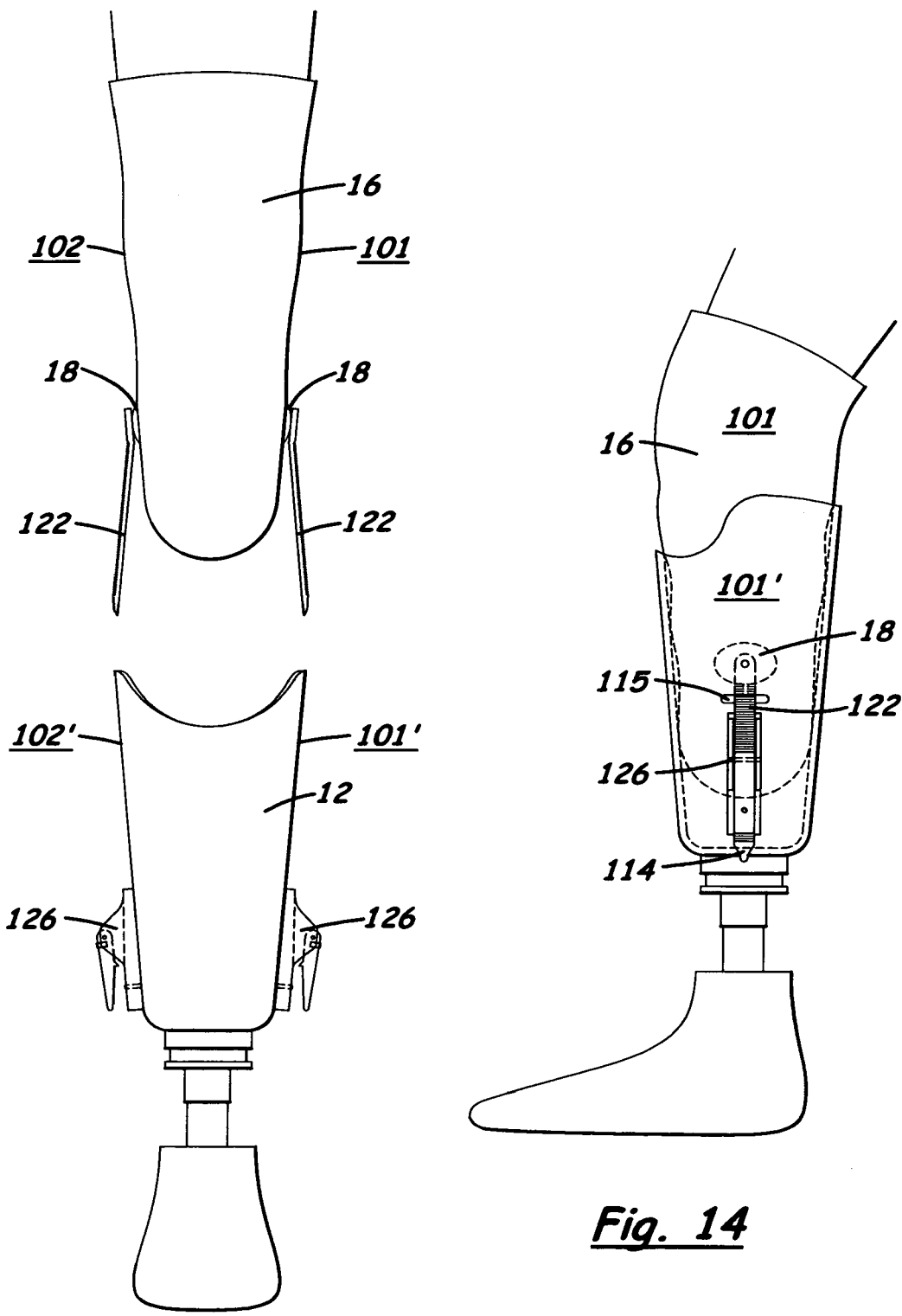
FIG. 13 is a ventral view of the especially preferred embodiment of the prosthetic attachment system showing two straps located laterally and medially.
FIG. 14 is a close-up, lateral view of the especially preferred embodiment of the prosthetic attachment system of FIG. 13.
Figure 17:
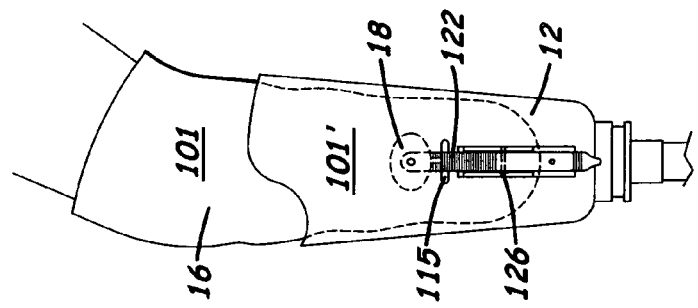
FIGS. 15–17 are sequential, lateral views of the especially preferred embodiment of the prosthetic attachment system of FIGS. 13 and 14 depicting the process of installing a prosthetic on a residual limb.

In the Description and Claims, the term "lateral" means on/toward the outer surface or region of the body, and therefore, on/toward the outer surface or region of the apparatus that is installed on the human body. Thus, a lateral surface of the liner or socket is an outer side surface, away from the inner or medial plane of the body. See lateral surfaces 101, 101' of the liner and socket, respectively, in FIGS. 13 and 14, wherein the apparatus is on the left leg and FIG. 13 is a ventral (front) view. The term "medial" means on/toward the inside or medial plane of the body. Thus, a medial surface of the liner or socket is an inner side surface, away from the outside of the body. See medial surfaces 102, 102' of the liner and the socket, respectively, in FIG. 13, wherein the apparatus is on the left leg.

The especially preferred embodiment comprises one or more attachment systems having improved straps and latch mechanisms that make donning and doffing the prosthesis more convenient and comfortable. The embodiment of FIGS. 13–17 comprises two straps 122, one attached to the lateral surface 101 of the liner 16 and one attached to the medial surface 102 of the liner 16, as shown in FIG. 13. These two straps are secured to the liner by means of an umbrella 18 described above and shown in FIGS. 1–12B.

The especially preferred strap 122 has a "nipple" shaped tab extension 114, or other tapered, narrow tip, at its distal end. The extension 114 preferably has a width less than half of the width of the strap 122. The extension facilitates the strap122 from the inside of the socket 12 to the socket's external surface and through the buckle 126 (see FIG. 19). The bottom surface 123 of the especially preferred strap 122 may have a longitudinal channel 124, or other grove or ramp-like shape at the distal end, to prevent the strap 122 from "catching" on the rivet 20 in the base 110 of the buckle 126. The thinness (from top surface to bottom surface) of the central region of the distal end, caused by the channel 124, aids in smooth insertion of the strap 122 into the buckle 126, and allows the distal end to slide over the rivet 20. This way, the rivet 20 need not be lowered or countersunk into the base 110. Alternatively, the entire bottom surface of the distal end of the strap may be slanted/thinned, but this would result in a weaker distal end.

Figure 16:
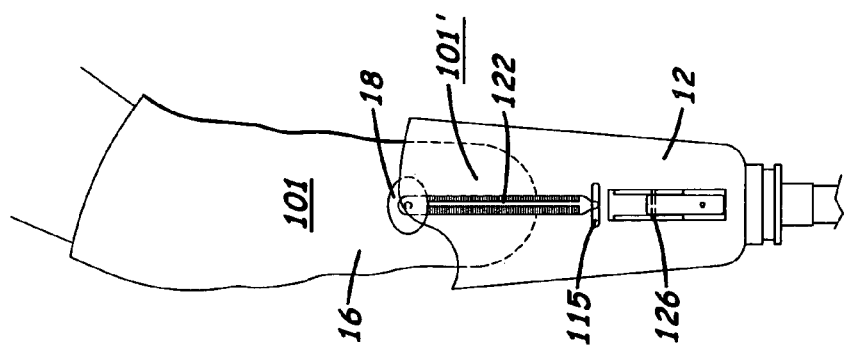
Figure 15:
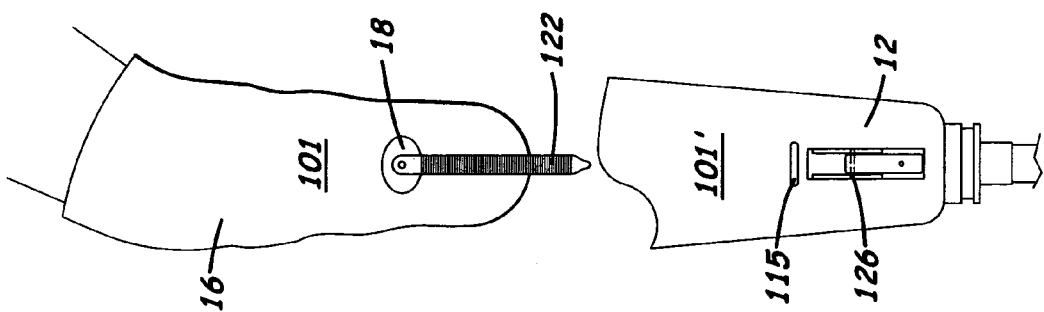

In order to install the socket 12 on the residual limb, the user places the two straps 122 inside the socket 12 and then feeds them through two apertures 115 located medially and laterally in the socket's 12 side wall, as seen in FIGS. 15 and 16. Once the tabs 114 of the straps 122 exit the apertures 115 to the external surface of the socket 12, they feed into two buckles 126, distal from the apertures 115, on the medial and lateral surface of the socket 12 (see FIGS. 16 and 17). The especially preferred buckle 126 may include a spring-biased member with one or more sharp edges 113, that frictionally engage transverse detents 17 located between transverse raised ridges on the strap's surface. Connected to each base 110 of the buckles 126, are a lever 111, pivot axle pin 111', and e-clips 111" or other biasing spring or member, which together create a biased system for receiving and capturing the straps 122. The top surface of each base 110 ramps up towards the distal end of the buckle 126, allowing easy insertion of the straps 122, as shown in FIG. 18. As the distal end of each strap 122 moves into the proximal end of each buckle 126, the sharp edge or edges 113 of the buckles 126 engage the transverse detents 17 of the straps 122 (see FIG. 19). The channel 124, on each strap 122, bypasses the rivet 20 in base 110 of its respective buckle 126, allowing the distal end strap 122 to exit the distal end of the buckle 126, in turn securing the socket 12 to the residual limb (see FIG. 19).

The especially preferred method for releasing the straps 122 from the buckles 126, is for the user to pull up on the distal end of each lever 111 to pivot the lever 111 into a raised position as shown in FIG. 18A, which corresponds to pivoting the distal end of the lever 111 away from the socket. This, in turn, disengages the sharp edge or edges 113 of each buckle 126 from the transverse detents 17 of each strap 122 (see FIGS. 18 and 19). The user is then able to remove the socket 12 from the residual limb by holding on to each lever 111 and pulling the socket 12 off the liner and also by maneuvering his/her residual limb out of the socket. Having a plurality of attachment systems for a single prosthetic device may improve stability and comfort for the user. By utilizing lateral and medial strap and buckle combinations, rotation of the prosthetic device relative to the user's residual limb is minimized, if not prevented. Further, the levers of the lateral and medial buckles provide a hand-hold for the user, especially during removal of the socket from the liner-covered residual limb. The lift-to-release bucket levers may be easier to operate and may provide a better hand-grip for the user, compared to the embodiment of FIGS. 1–12B which requires that the user push and hold down the levers of the buckles during removal of the prosthesis.

While lateral and medial positions for two strap and buckle combinations are preferred, other locations and other numbers of strap and buckle combinations are also possible. The buckles in FIG. 13 are depicted to be quite large and to protrude significantly from the socket, the buckles may be made to be small and low-profile, so that the strap and buckle combination is discreet when covered by clothing and comfortable for walking without the buckle catching on the other leg or clothing. Preferred levers 11 and 111 are deemed to be convenient and reliable for latching and unlatching their respective buckles, and preferably, each lever is biased into the latched position and requires positive action by the user or prosthetist to unlatch it. However, other styles of latch mechanisms may be used, such as other pivotal arms or hooks, snaps, clips, or other releasable locks and latches.

Preferably, the prosthesis attachment system comprises the invented extension member and latch system, with or without the aid of suction between the liner and the socket, but no other straps or attachments. Preferably, there is no belt or strap extending to encircle part of the user's body, and preferably no attachment between the distal end of the limb/liner and the bottom of the well of the socket.

Although this invention has been described above with reference to particular means, materials and embodiments, it is to be understood that the invention is not limited to these disclosed particulars, but extends instead to all equivalents within the broad scope of this disclosure and the following claims.

What we claim is:

1. An attachment system for a prosthesis comprising:
   a prosthesis having a socket with a side wall surrounding and defining an interior well for receiving a user's residual limb;
   a roll-on liner adapted to attach to a user's residual limb by surrounding the residual limb, the roll-on liner being received in the socket;
   an extension member passing from the roll-on liner through the socket side wall and connecting to an outer side surface of the socket; and,
   a latch mechanism with a pivotal arm and a bias member, and the extension member further comprises a strap having transverse teeth in its upper surface and detents between said teeth,
   wherein the strap slides through the latch mechanism and is retained in the latch mechanism by the pivotal arm being biased into said detents.

2. An attachment system as in claim 1, wherein said pivotal arm has a pivot axis and extends distally from said pivot axis and is adapted to be pivoted away from said socket to release the strap from the latch mechanism.

3. An attachment system for a prosthesis comprising:
   a prosthesis having a socket with a side wall surrounding and defining an interior well for receiving a user's residual limb;
   a roll-on liner adapted to attach to a user's residual limb by surrounding the residual limb, the roll-on liner being received in the socket;
   an extension member passing from the roll-on liner through the socket side wall and connecting to a outer side surface of the socket;
   the attachment system further comprising a latch mechanism receiving and latching onto the extension member, and wherein the extension member further comprises a strap with a longitudinal axis, a width transverse to the longitudinal axis, and an extension at a distal end of the strap. the extension having a width that is less than half of the width of the strap; and,
   wherein said extension has a longitudinal channel with a ramped bottom wall.

4. An attachment system for a prosthesis, comprising:
   a liner adapted to fit over the residual limb of a user, said liner having a proximal region and a distal end, and an outside surface adapted to extend circumferentially all the way around the residual limb;
   a strap secured to the proximal region of said liner's outside surface, said strap extending towards the distal end of said liner;
   a socket for fitting over said liner and said residual limb, said socket having a proximal end and a distal end, an inside surface, and an outside surface;
   an aperture in said socket for allowing said strap to pass from the inside surface of the socket to the outside surface of the socket, said aperture being placed proximally on said socket; and
   a lock mechanism on the outside surface of said socket for receiving and securing said strap; and,
   wherein said strap has a plurality of transverse detents on the top surface thereof.

5. An attachment system according to claim 4 wherein said lock mechanism comprises a buckle device with a spring-biased lever with a sharp edge for engaging one of said transverse detents.

6. An attachment system for a prosthesis, comprising:
   a liner adapted to fit over the residual limb of a user, said liner having a proximal region and a distal end, and an outside surface adapted to extend circumferentially all the way around the residual limb;
   a strap secured to the proximal region of said liner's outside surface, said strap extending towards the distal end of said liner;
   a socket for fitting over said liner and said residual limb, said socket having a proximal end and a distal end, an inside surface, and an outside surface;
   an aperture in said socket for allowing said strap to pass from the inside surface of the socket to the outside surface of the socket, said aperture being placed proximally on said socket; and
   a lock mechanism on the outside surface of said socket for receiving and securing said strap; and,
   wherein said lock mechanism comprises a ratchet buckle with a lever at its distal end, the lever being pivotal into a latch position near the socket wherein it secures the strap in the lock mechanism, and pivotal into an unlatch position away from the socket wherein it release the strap to slide out of the lock mechanism.

* * * * *